US008061356B2

(12) United States Patent
Bowen

(10) Patent No.: US 8,061,356 B2
(45) Date of Patent: Nov. 22, 2011

(54) DIRECTIONAL FLAT FACE MASK

(75) Inventor: Michael L. Bowen, Richland Hills, TX (US)

(73) Assignee: Prestige Ameritech Ltd., Fort Worth, TX (US)

( * ) Notice: Subject to any disclaimer, the term of this patent is extended or adjusted under 35 U.S.C. 154(b) by 947 days.

(21) Appl. No.: 12/033,369

(22) Filed: Feb. 19, 2008

(65) Prior Publication Data

US 2009/0205666 A1 Aug. 20, 2009

(51) Int. Cl.
*A61M 11/00* (2006.01)

(52) U.S. Cl. .............................. 128/206.12; 128/206.21

(58) Field of Classification Search ............. 128/206.12, 128/206.19, 206.17, 206.21, 206.28, 205.25, 128/205.27

See application file for complete search history.

(56) References Cited

U.S. PATENT DOCUMENTS

| | | | | |
|---|---|---|---|---|
| 4,536,440 | A | 8/1985 | Berg | |
| 4,606,341 | A | 8/1986 | Hubbard et al. | |
| D287,649 | S | 1/1987 | Zdrok et al. | |
| 4,635,628 | A | 1/1987 | Hubbard et al. | |
| 4,802,473 | A | 2/1989 | Hubbard et al. | |
| 4,807,619 | A | 2/1989 | Dyrud et al. | |
| 4,920,960 | A | 5/1990 | Hubbard et al. | |
| 4,969,457 | A | 11/1990 | Hubbard et al. | |
| 5,025,506 | A | 6/1991 | Huang | |
| 5,307,796 | A | 5/1994 | Kronzer et al. | |
| 5,322,061 | A | 6/1994 | Brunson | |
| 5,701,892 | A | 12/1997 | Bledstein | |
| 6,234,171 | B1 * | 5/2001 | Springett et al. | 128/206.12 |
| 6,394,090 | B1 * | 5/2002 | Chen et al. | 128/206.12 |
| 2004/0000313 | A1 | 1/2004 | Gaynor et al. | |
| 2006/0289009 | A1 | 12/2006 | Palomo et al. | |
| 2008/0023006 | A1 * | 1/2008 | Kalatoor | 128/205.29 |

OTHER PUBLICATIONS

International Search Report, International Application No. PCT/US2009/034370, 2 pages, 2009.

Written Opinion of the International Searching Authority, International Application No. PCT/US2009/034370, 4 pages, 2009.

1 sheet face mask, web page: images.lowes.com.

* cited by examiner

*Primary Examiner* — Steven Douglas

(74) *Attorney, Agent, or Firm* — Geoffrey A. Mantooth

(57) ABSTRACT

A face mask has mask material and ties or ear loops coupled to the mask material. The face mask is flat until worn. The mask material has an outside and an inside, which inside is designed to be against the wearer's face when the mask is worn. A deformable nose strip is provided near a top edge of the mask material. The nose strip is preformed into a contour for fitting about a nose. The contour bows out from the inside to the outside. A wearer donning the mask intuitively knows to orient the contour to the wearer's nose, wherein the inside is automatically positioned against the wearer's face.

14 Claims, 5 Drawing Sheets

DIRECTIONAL FLAT FACE MASK

FIELD OF THE INVENTION

The present invention relates to flat face masks of the type used to filter contaminants relative to the wearer, as well as methods of making the same.

BACKGROUND OF THE INVENTION

Face masks are worn in medical environments, such as surgical operating rooms, in order to minimize the transfer of contaminants. In an operating room, the surgeons, nurses, and other personnel wear face masks so as to filter out contaminants from their breathing and to minimize the risk of infection to the patient undergoing the surgical procedure. In addition, the face masks serve to protect the medical personnel from infectious agents that may emanate from the patient.

Another use for face masks is in clean rooms. Such clean rooms are used, for example, in semiconductor manufacturing. The face masks reduce particle emissions from the human workers.

Early face masks were made of cloth and were sewn together. In the 1960's, masks began to be made from disposable non-woven fabrics. At first, the disposable fabrics were sewn; later the masks were made by ultrasonically bonding the materials to each other.

One general type of face mask is flat and is typically rectangular in shape. Flat face masks are typically pleated in the mask body to allow for some fitting of the mask to the curvature of a human face. A flat face mask can be of the 4-tie variety or the ear loop variety. In the 4-tie variety, ties extend out from the mask body which are then tied around the back of the wearer's head. The ear loop variety has elastic loops that fit around the ears of the wearer; no tying is needed.

The prior art flat face mask has a flat nose strip along the top edge. To use, the face mask is placed against the face, with the nose strip located on the bridge of the nose. The user presses the nose strip to form a contour around the nose.

Another type or style of face mask is the "cone" or "cup-shaped" mask, which is a molded bowl-shaped mask with an elastic band that extends around the back of a wearer's head. Such cone masks are described in U.S. Pat. Nos. 4,807,619 and 4,536,440. They have a shaping layer of thermally bonded fibers, which layer provides the cone shape. The shaping layer is made by molding webs of thermally bonding fibers in heated molds, which molds are at temperatures above the softening point of the thermally bonding fibers.

Flat face masks typically have a body with three layers, namely an outer layer, a middle filtration layer and an inner layer. The inner layer is chosen so as to be comfortable on the skin. The outer layer can irritate the skin. Therefore, it is desirable to properly orient the mask to the skin, so that the inner layer is against the skin. In addition, the face mask typically has a fluid resistant layer and has an anti-microbial layer. These fluid resistant masks and anti-microbial masks perform satisfactorily only if they are worn correctly, with the outer layer on the outside and the inside layer against the wearer.

Identifying the proper orientation of a flat face mask has proven difficult. People frequently don a flat face mask with the inner layer facing out, in an inside out orientation.

In many masks, the inner and outer layers are the same color, making identification of the inside particularly difficult. In some prior art flat face masks, the inner layer and outer layer are different colors. Even with this color differentiation however, problems persist in correctly donning the face mask.

Furthermore, some prior art face masks have the word "inside" imprinted on the inner layer. However, health care workers still don the masks inside out.

SUMMARY OF THE INVENTION

The present invention provides a method of making a flat face mask. A panel of mask material is provided. The mask material has an outside and an inside, with the inside structured and arranged to be adjacent to a wearer's face. A deformable nose strip is provided adjacent to the mask material. The nose strip is pressed into a contour, with the outside of the contour being convex and the inside of the contour being concave, while retaining the substantially flat shape of the remainder of the mask. The face mask is then packaged.

In accordance with one aspect of the present invention, the flat face mask has an area without thermal bonding so as to retain flexibility.

In accordance with still another aspect of the present invention, a fluid resistant layer is provided in the mask material.

In accordance with still another aspect of the present invention, an anti-microbial agent is provided in the mask material.

In accordance with still another aspect of the present invention, the step of pressing the nose strip into a contour further comprises positioning the nose strip and adjacent mask material into a press, closing the press on the nose strip and forming the contour and then opening the press and removing the face mask.

In accordance with another aspect of the present invention, the nose strip is pressed into a contour by moving the face mask through forming rollers.

In accordance with another aspect of the present invention, the face masks are stacked so as to nest the nose contours.

The present invention also provides a method of donning a flat face mask. A flat face mask is provided with an inside and an outside and a preformed nose contour that bows to the outside. The face mask is oriented to a face so that the nose contour is aligned with a nose on the face, wherein the inside face is the face. The face mask is contacted with the face, with the contour fitted onto the nose.

In accordance with another aspect of the present invention, the face mask is fastened to a wearer's head.

In accordance with still another aspect of the present invention, after contacting the face mask with the face and fitting the contour onto the nose, pressing the nose strip to further shape the contour to the nose.

The present invention also provides a stack of flat face masks. Each face mask has an inside and an outside and side edges. Each face mask is generally flat with the exception of a contoured nose portion that bows in the direction of the outside. The face masks are stacked so that the contoured nose portions are nested, wherein the insides of the face masks all face in the same direction.

In accordance with another aspect of the present invention, the stack is oriented so that the outsides of the face masks are up.

In accordance with another aspect of the present invention, packaging surrounds the stack of face masks.

In accordance with still another aspect of the present invention, the face masks have an area without thermal bonding.

DESCRIPTION OF THE PREFERRED EMBODIMENT

Figure 1:
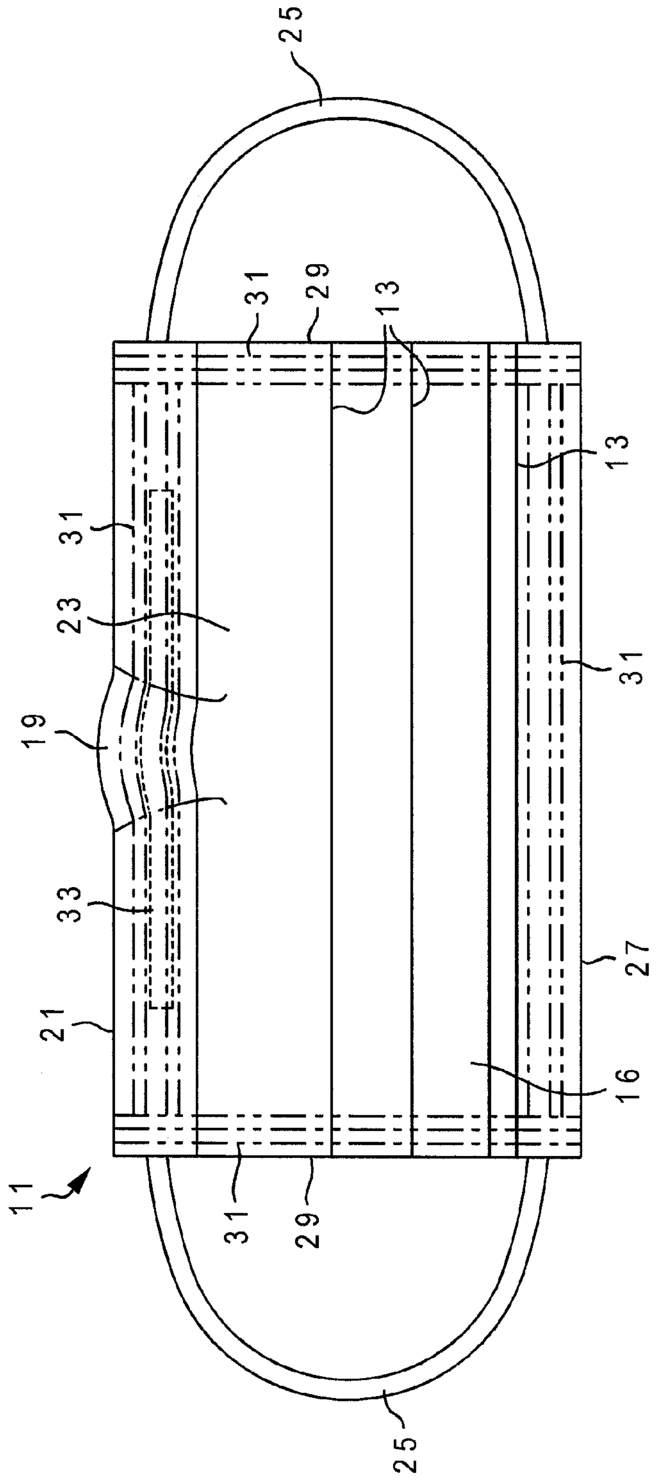
FIG. 1 is a plan view of the outside of a face mask of the present invention, in accordance with a preferred embodiment.

In FIG. 1, there is shown a flat face mask 11 of the present invention. The face mask 11 is flat and is of the same type shown and described in U.S. Pat. Nos. 4,802,473 and 4,941,470, the complete disclosures of which are incorporated herein by reference. When not worn, the mask lays flat on a planar surface.

The face mask 11 is designed to be worn over the mouth and nose of a human. In order to allow the flat mask to bend or curve on the face contours, the face mask is formed of pleated material. The pleats 13 allow the mask to expand in a central area of the mask so as to fit over the nose and mouth (and sometimes chin) of the wearer. The face mask is also provided with loops 25 to fit around the ears of a human.

The face mask of the present invention is a flat face mask. The mask is flat before being used; once used, the mask is bent to conform to the wearer's face. The face mask 11 is more flexible than a cone-shaped mask. A cone-shaped mask has a shaping layer of thermally bonding fibers. The shaping layer has been heated and molded into the cone shape. When cooled, the shaping layer retains its shape. The shaping layer extends across all areas of the cone-shaped mask. The cone mask retains its cone shape, even if laid on a flat surface. Conversely, the flat face mask 11 has areas 31 of thermal bonding and one or more areas 16 without thermal bonding. The areas 31 of thermal bonding are typically along the edges of the flat face mask, while the area 16 without thermal bonding is typically between the edges. The area 16 without thermal bonding is flexible and soft feeling. Contrastingly, the cone shape mask feels "starchy" with more stiffness than the "unstarched" non-thermal bonded area 16 of the flat face masks. The area 16 without thermal bonding does not retain a curved shape. Instead, when the mask is laid on a flat surface, the mask will also be flat. In the flat face mask 11, the bonded areas 31 are more flexible than the shaping layer of a cone-shaped mask. Thus, even the bonded areas 31 also feel "unstarched" when compared to the starched feel and stiffness of a cone-shaped mask. The bonded areas 31 are flexible because the thermal bonding is discontinuous; for example the thermal bonding is in a pattern of dashes.

Although the face mask is shown and described herein as pleated, it need not be so; the face mask can be unpleated.

As will be explained in further detail below, the face mask shown in FIG. 1 has a single panel, or portion, which panel can be made of one or more layers. The face mask of the present invention can have more than one panel or portion. For example, the face mask can have upper and lower portions joined together in a "duckbill" configuration, as shown in U.S. Pat. No. 5,322,061. The mask is flat until it is used. The face mask can also be of the type shown in U.S. Pat. No. 4,606,341 which has a single trapezoidal pleat. This mask is also flat until used.

In addition, the face mask of the present invention can be provided with ear loops 25 as shown in FIG. 1, or with ties as shown in U.S. Pat. No. 4,606,341, the entire disclosure of which is incorporated herein by reference.

Figure 2:
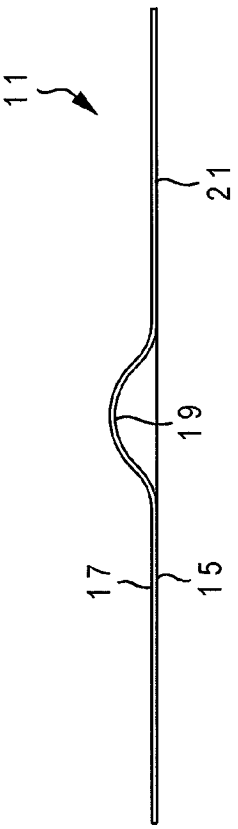
FIG. 2 is a view of the top edge of the face mask.

The face mask has an inside 15 and an outside 17 (see FIG. 2). The inside 15 is designed to be in contact with the wearer's face.

Referring to FIGS. 1 and 2, the face mask 11 has a nose contour 19 located at a top edge 21 of the mask. The nose contour 19 is preformed and fits around the nose of the wearer. In prior art face masks, the mask, including the top edge, is flat. To use a prior art face mask, a person places the face mask against the face and bends the top edge into a contour around the nose.

With the face mask of the present invention, the top edge of the face mask is already shaped to fit around a nose (see FIG. 2). The nose contour 19, or notch, is formed so that the wearer will orient the face mask in the proper direction, with the inside of the mask against the wearer's face. The nose contour 19 thus minimizes the possibility that the wearer will don the face mask inside out.

The face mask 11 will now be described in more detail. The face mask 11 comprises a panel of mask material 23 and ties or ear loops 25 that hold the mask on a wearer's head.

The mask material 23 can be one or more layers. In one embodiment, the mask material has three layers, namely an inside layer, an intermediate layer and an outside layer. In the description of the mask, terms such as "inside" and "outside" refer to the orientation of the mask when worn; the "inside" is against the wearer's face, while the "outside" is exposed. The inside layer can be wet laid cellulose, tissue or a copolymer such as bico (bicomponent polymers). The intermediate layer is a filter media and can be melt-blown polypropylene or melt-blown polyester. The outside layer can be spun-bonded polypropylene or tissue or a breathable plastic. Even though the intermediate layer is the primary filter media, all of the layers form a filter media to some extent. More than three layers can be provided. For example, a fourth plastic layer can be provided. In addition, binding strips can be provided as additional layers.

The face mask may also contain a fluid-resistant layer. The layer could be a fluid-resistant breathable film. Such a film is conventional and commercially available. The layer is a barrier material and is able to differentiate between gasses and liquids. Barrier materials have small apertures which prevent liquids from passing therethrough due to the liquid's relatively high surface tension. The barrier material typically passes gasses freely in either direction (from inside to outside and from outside to inside), while restricting the passage of liquids in at least one direction.

The face mask may contain an anti-microbial layer, which layer has an anti-microbial agent. Such anti-microbial agents are conventional and commercially available. As an example, the agent may be iodine-based.

The fluid resistant layer could be an intermediate layer. Likewise, the anti-microbial layer could be an intermediate layer.

Referring to FIG. 1, the mask 11 has a top edge 21, a bottom edge 27 and side edges 29. The mask material 23 is pleated 13. The pleats 13 form folds and extend from one side edge 29 to the other side edge 29.

The layers of the mask material are coupled or bonded together at the side edges 29 and at the top and bottom edges 21, 27 so as to form a panel. In the preferred embodiment, the layers are coupled together by ultrasonic bonding. The bonded areas 31 extend in from the edges and are illustrated in the drawings by lines with a dash-dot-dot pattern.

The mask material is flexible and lacks the stiffness of a "cone" mask. A cone mask is molded into a bowl shape and retains its shape. Therefore, the material making up a cone mask is stiff so as to hold its shape. The flat mask will not retain a shape if bent.

The top edge 21 has a semi-rigid or malleable nose strip 33 located therein. The nose strip 33, which may made of aluminum, fits around the nose of the wearer. The nose strip 33 is deformable. The nose strip 33 is typically located between the inside layer and a finish layer. In one embodiment, the inside layer can be folded over the top edge 21 so as to form the finish layer and overlie a portion of the outside layer. Also, the inside layer can be folded over the bottom edge 27 so as to overlie a portion of the outside layer. In another embodiment, the finish layer is a separate binding layer or strip, which separate binding layer can be made of the same material as either the outside or inside layers. A separate binding strip can also be provided along the bottom edge 27.

In the preferred embodiment, the face mask has either ties or ear loops 25. The ear loops are only shown in FIG. 1. The ear loops 25 are an elastic knitted material or a plastic elastomer. The ear loops 25 have ends that are coupled to the mask. The ends are ultrasonically bonded to the mask. Alternatively, ties could be provided, which ties could be made from bindings extending from the top and bottom edges, as are found in 4-tie masks.

To make the face mask, the layers of the mask material 23 are brought together, pleated and then bonded at the edges 21, 27, 29. The edges can be bonded together by ultrasonic bonding, by heat and pressure or by adhesives.

The layers of the mask material are provided in continuous webs, typically contained on rolls. The layers are unrolled and brought together and bonded in a continuous process. In the continuous process, the web of mask material 23 moves through the manufacturing process or line, without stopping. At one station along the manufacturing line, the layers are brought together. At another station further down the manufacturing line, the layers are pleated. At still another station, the layers are bonded together at the edges 21, 27, 29. In the preferred embodiment, the edges are bonded together using ultrasonic energy. The side edge 29 of the mask material 23 is located between an ultrasonic horn and an anvil, which can be rectangular, cylindrical, etc. The horn and anvil are brought together to clamp the edge of the mask material.

In the next step of fabrication of the mask, the mask material 23 is cut into separate masks. Then, the ear loops 25 are attached to the mask.

When the nose strip 33 is put into the mask, the nose strip 33 is flat. The mask material 23 is also flat. Even though the mask material may have pleats, or several panels, the mask material is generally flat.

Figure 3A:
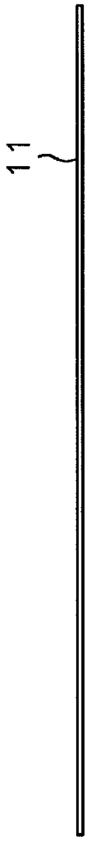
FIGS. 3A-3C illustrate steps of the manufacture of the face mask.
Figure 3B:
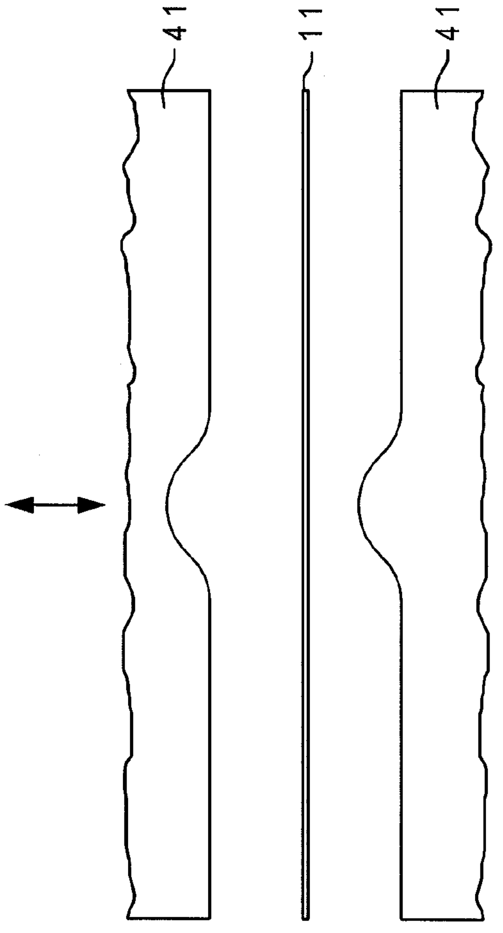
Figure 3C:
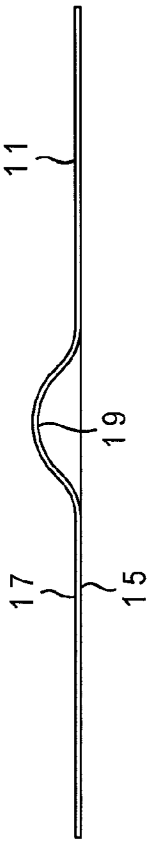

The nose strip 33 is molded into a contour or notch. One way to accomplish this is by passing the face mask through a press, which press is shaped in the desired contour. Referring to FIGS. 3A-3C, in the first step (FIG. 3A), the flat face mask is positioned to go into the press 41. Next, in FIG. 3B, the face mask is positioned inside of the open press 41. The press is then closed onto the face mask, bending the nose strip into the desired contour. The press is then opened and the face mask is removed (see FIG. 3C).

The step of contouring the nose strip can be at any time after the layers are bonded together. For example, the nose strip can be contoured either before or after the ear loops are attached and either before or after the mask material is cut into separate masks.

Figure 7:
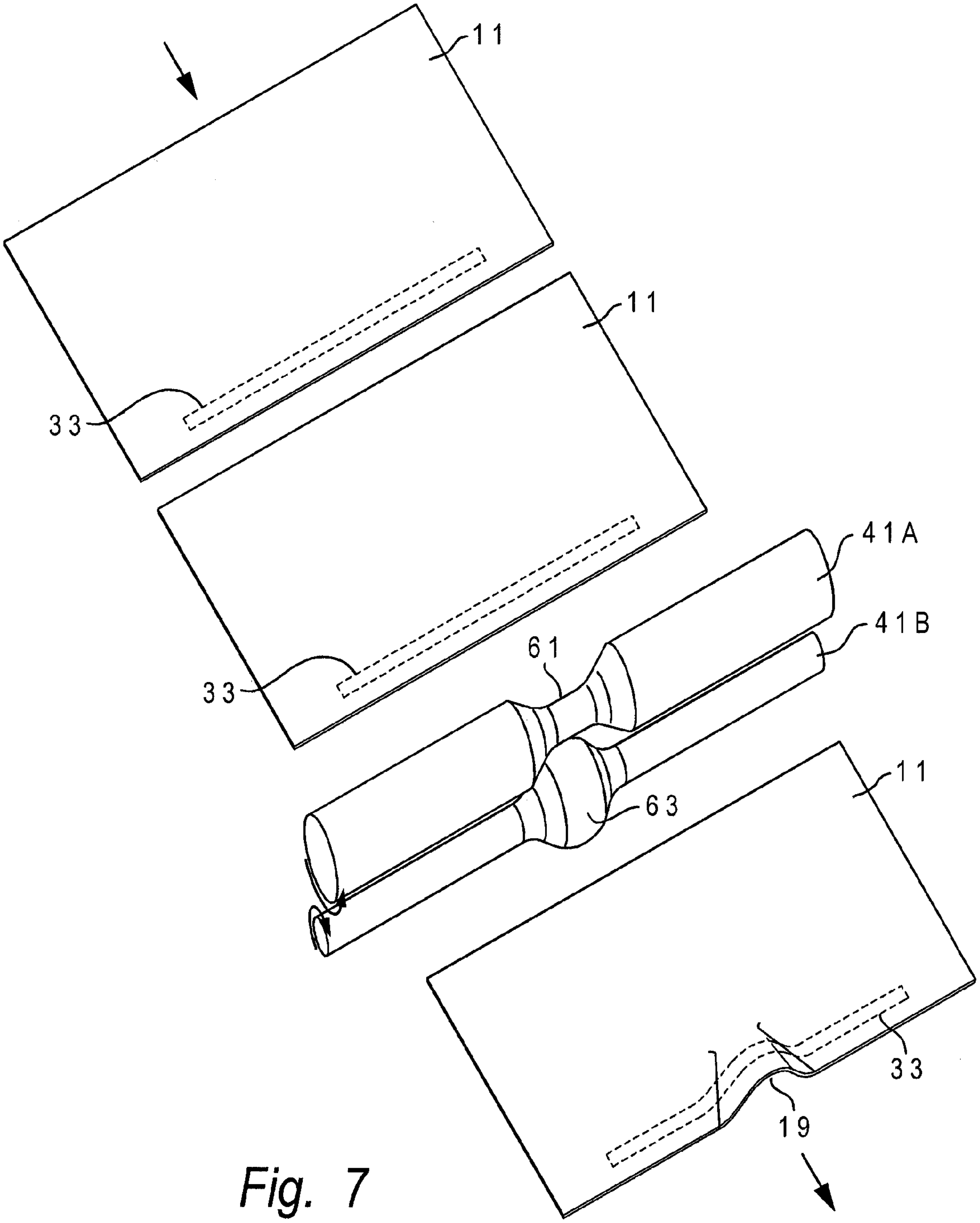
FIG. 7 is a perspective view of face masks passing through contouring rollers.

Another way of contouring the nose strip 33 is to pass the mask through a set of contouring or forming rollers 41A, 41B (see FIG. 7). One forming roller 41A is provided with a circumferential cavity 61, while the other forming roller 41B is provided with a corresponding circumferential protrusion 63. As the mask 11 passes through the rollers, such that the nose strip is parallel to the rotational axes of the rollers, the nose strip is pressed into the desired contour by the cavity 61 and the protrusion 63. The rest of the mask passes through the rollers. However, the remainder of the mask returns to the flat shape, while the malleable nose strip retains the contour.

The nose contour 19 is bowed, or bulges, to the outside (see FIG. 2). Thus, on the outside, the nose contour 19 is convex, while on the inside, the nose contour is concave. This forms a recess on the inside of the mask, which recess receives the nose. The nose contour 19 extends from the top edge 21 toward the bottom edge 27. The nose contour 19 need not extend all the way to the bottom edge 27.

The face mask 11, even with the nose contour 19, is still largely flat.

Figure 4:
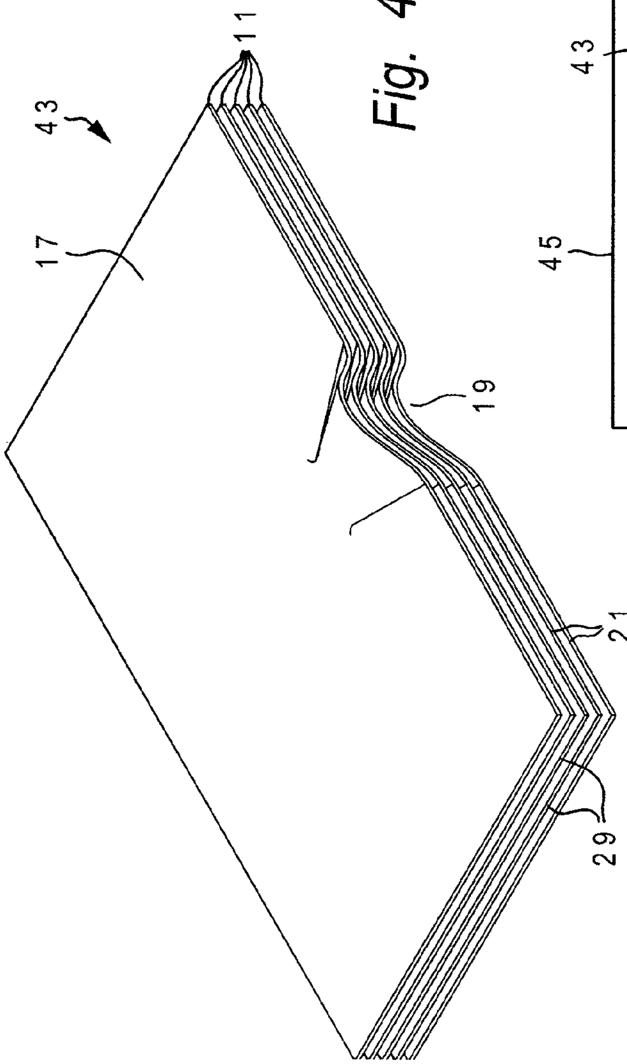
FIG. 4 is a perspective view of a stack of the face masks.

The contoured face masks 11 may be stacked, as shown in FIG. 4. The nose contours 19 make for easy stacking in that the nose contours are nested and the edges 21, 27, 29 are aligned. Stacking also better preserves the nose contour 19 as the contour is less likely to be accidentally flattened when in a stack. Preferably, the stack 43 has the outside 17 of the face masks facing up, as shown in FIG. 4. This keeps the insides 15 cleaner. The face masks are stacked in a desired quantity, such as fifty.

Figure 5:
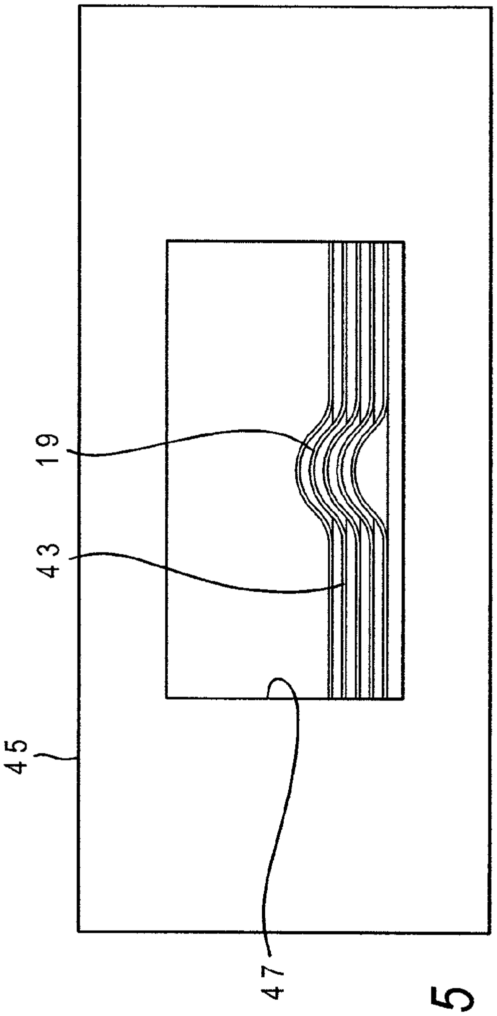
FIG. 5 is a front elevational view of a box of a stack of the face mask.

The stack 43 of face masks is then packaged. For example, the stack of face masks is located inside of a box 45 (see FIG. 5). The box is generally rectangular with a top that can be opened. The front side of the box can have a window 47 to allow viewing of the face masks inside. This also give an indication of the quantity of face masks left inside of the box, which allows a user to determine if the box is almost empty. Individual face masks 11 can be packaged as well. Packaging provides protection for the face mask, retaining the shape of the nose contour and keeping the mask clean.

Figure 6:
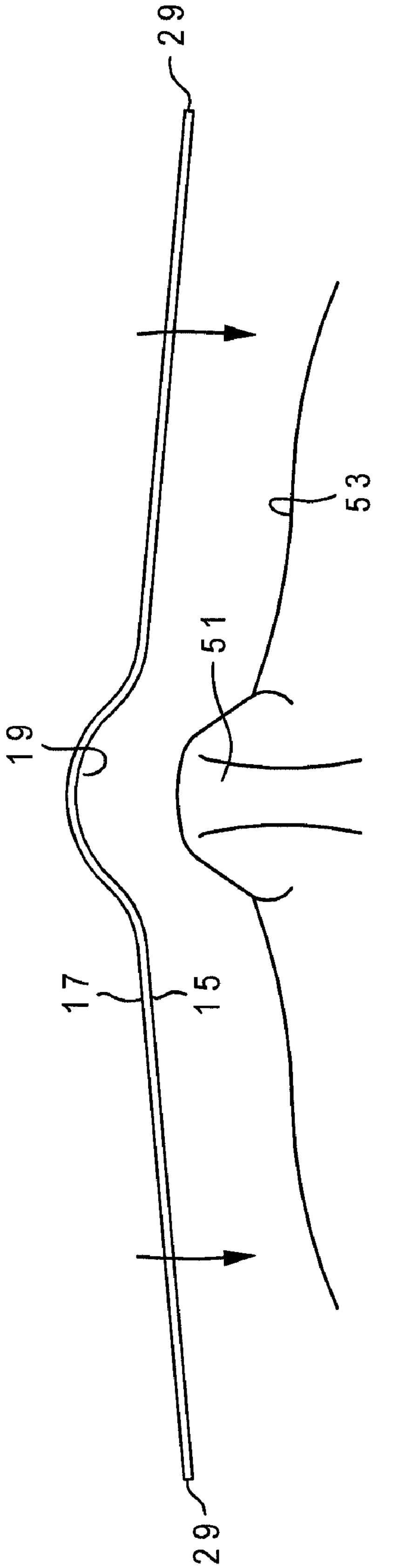
FIG. 6 is a view of the top edge of a face mask being donned onto a face.

To use the face mask 11, the user or wearer grasps the topmost mask from the stack 43. The user orients the mask with the nose contour 19 at the top and the nose contour extending out, so as to match the bridge of the nose 51 (see FIG. 6). The wearer then places the mask against the face 53, with the contour 19 fitting around the nose 51. The nose strip 33 typically crosses the bridge of the nose. The ear loops are looped around the wearer's ears, pulling the side edges 29 of the mask into the face 53. If the nose contour 19 needs to be adjusted to fit around the nose, the wearer presses the nose strip 33 into the proper fit around the nose. Thus, the nose strip 33 is finely adjusted once fitted onto the nose. The mask is now ready.

With the contoured nose strip, the inside 15 of the mask is placed against the wearer's face 53. Thus, the mask 11 is properly oriented, ensuring that all fluid resistant layers or anti-microbial layers will work properly. The nose contour 19 provides a subtle clue for instructing the user as to the proper direction and orientation of the face mask. The user need not look for any "inside" label or sign, or remember which color goes in or out.

In addition, the nose contour 19 saves time and effort as the mask fits to the face and nose at once, without any adjustment. Thus, a wearer who is in a hurry can quickly don a mask and not use a hand to press the nose strip into the contour around the nose, as with a prior art flat face mask.

The foregoing disclosure and showings made in the drawings are merely illustrative of the principles of this invention and are not to be interpreted in a limiting sense.

The invention claimed is:

1. A method of making a flat face mask, comprising the steps of:

a) providing a panel of mask material, the mask material having an outside and an inside, the inside structured and arranged to be adjacent to a wearer's skin;

b) providing a deformable nose strip adjacent to the mask material;

c) pressing the nose strip into a contour, with the outside of the contour being convex and the inside of the contour being concave, while retaining the substantially flat shape of the remainder of the mask;

d) after pressing the nose strip into a contour, packaging the face mask.

2. The method of claim 1 wherein the flat face mask has an area without thermal bonding so as to retain flexibility.

3. The method of claim 1 further comprising the step of providing a fluid resistant layer of mask material.

4. The method of claim 1 further comprising the step of providing an anti-microbial layer of mask material.

5. The method of claim 1 wherein the step of pressing the nose strip into a contour further comprises the steps of:

a) positioning the nose strip and adjacent mask material into a press;

b) closing the press on the nose strip and forming the contour;

c) opening the press and removing the face mask.

6. The method of claim 1 wherein the step of pressing the nose strip into a contour further comprises the step of moving the face mask through forming rollers.

7. The method of claim 1 further comprising the steps of stacking the face masks so as to nest the contoured nose strips.

8. A method of donning a flat face mask, comprising the steps of:

a) providing a stack of flat, unfolded face masks, with each face mask having an inside and an outside and a pre-formed nose piece that is contoured as convex on the outside and concave on the inside, with the outside of one face mask adjacent to the inside of the adjacent face mask;

b) removing one of the face masks from the stack;

c) orienting the one face mask to a face so that the nose piece is aligned with a nose on the face, wherein the inside faces the face;

d) contacting the face mask with the face, with the nose piece fitted onto the nose.

9. The method of claim 8 further comprising the steps of fastening the face mask to a wearer's head.

10. The method of claim 8, further comprising the steps of, after contacting the face mask with the face and fitting the contour onto the nose, pressing on the nose strip to further shape the contour to the nose.

11. A stack of flat face masks, comprising:

a) each face mask having an inside and an outside and side edges, each face mask being generally flat with the exception of a contoured nose piece, with the outside of the piece being convex and the inside of the piece being concave;

b) the face masks are stacked so that the contoured nose pieces are nested, wherein the insides of the face masks all face in the same direction.

12. The stack of face masks of claim 11, wherein the stack is oriented so that the outsides of the face masks are up.

13. The stack of face masks of claim 11, further comprising packaging that surrounds the stack of face masks.

14. The stack of face masks of claim 11, wherein each face mask has an area without thermal bonding.

* * * * *